(12) United States Patent
Van Ingelgem et al.

(10) Patent No.: US 8,777,916 B2
(45) Date of Patent: Jul. 15, 2014

(54) TAMPON APPLICATOR ASSEMBLY

(75) Inventors: Werner Van Ingelgem, Zele (BE); Annick De Poorter, Zele (BE); Steven Smet, Zele (BE)

(73) Assignee: Ontex Hygieneartikel Deutschland GmbH, Grosspostwitz (DE)

( * ) Notice: Subject to any disclaimer, the term of this patent is extended or adjusted under 35 U.S.C. 154(b) by 220 days.

(21) Appl. No.: 11/909,250

(22) PCT Filed: Mar. 7, 2006

(86) PCT No.: PCT/EP2006/002075
§ 371 (c)(1),
(2), (4) Date: Sep. 20, 2007

(87) PCT Pub. No.: WO2006/099944
PCT Pub. Date: Sep. 28, 2006

(65) Prior Publication Data
US 2008/0195029 A1    Aug. 14, 2008

(30) Foreign Application Priority Data
Mar. 25, 2005    (EP) .................................... 05447065

(51) Int. Cl.
*A61F 13/20* (2006.01)
*A61F 13/32* (2006.01)
*A61F 13/26* (2006.01)

(52) U.S. Cl.
CPC ........... *A61F 13/263* (2013.01); *A61F 13/2034* (2013.01)
USPC ........................................ 604/385.17; 604/16

(58) Field of Classification Search
CPC ............................ A61F 13/263; A61F 13/2034
USPC ................... 604/385.17–385.18, 904, 11–18
See application file for complete search history.

(56) References Cited

U.S. PATENT DOCUMENTS

| | | | |
|---|---|---|---|
| 435,491 A | | 9/1890 | Fredigké |
| 1,731,665 A | | 10/1929 | Huebsch |
| 1,941,717 A | | 1/1934 | Rabell |
| 1,964,911 A | * | 7/1934 | Haas .............................. 604/377 |
| 2,263,909 A | | 11/1941 | Webb |
| 2,355,628 A | * | 8/1944 | Calhoun ......................... 604/15 |
| 2,425,004 A | | 8/1947 | Rabell |
| 2,444,528 A | | 7/1948 | Popper et al. |

(Continued)

FOREIGN PATENT DOCUMENTS

| | | |
|---|---|---|
| AU | 2006263937 | 1/2007 |
| DE | 3 934 153 | 4/1991 |

(Continued)

OTHER PUBLICATIONS

International Search Report dated May 22, 2006.

(Continued)

*Primary Examiner* — Melanie Hand
*Assistant Examiner* — Paula L Craig
(74) *Attorney, Agent, or Firm* — Knobbe, Martens, Olson & Bear LLP

(57) ABSTRACT

A tampon applicator assembly is described which has a compact tampon applicator and a tampon having a longitudinal body defining an insertion end, a withdrawal end, a central section extending there between, a longitudinal axis, and an outer surface. The outer surface of the tampon has at least one area of radial depression.

21 Claims, 4 Drawing Sheets

(56) References Cited

U.S. PATENT DOCUMENTS

| | | | |
|---|---|---|---|
| 2,499,414 A | 3/1950 | Rabell | |
| 2,652,056 A * | 9/1953 | Lay | 604/365 |
| 2,706,986 A | 4/1955 | Carrier | |
| 2,798,260 A * | 7/1957 | Niepmann et al. | 28/119 |
| 2,965,101 A | 12/1960 | Schirmer et al. | |
| 3,011,495 A | 12/1961 | Brecht | |
| 3,013,558 A | 12/1961 | Leupold | |
| 3,101,713 A * | 8/1963 | Sargent | 604/16 |
| 3,138,159 A | 6/1964 | Schmidt | |
| 3,148,680 A * | 9/1964 | Roberts et al. | 604/18 |
| 3,196,873 A * | 7/1965 | Bletzinger et al. | 604/15 |
| 3,397,695 A | 8/1968 | Voss | |
| 3,431,909 A | 3/1969 | Krusko | |
| 3,610,243 A | 10/1971 | Jones, Sr. | |
| 3,643,661 A | 2/1972 | Crockford | |
| 3,696,812 A * | 10/1972 | Jaycox | 604/18 |
| 3,717,149 A * | 2/1973 | Morane | 604/12 |
| 3,834,389 A | 9/1974 | Dulle | |
| 3,981,305 A | 9/1976 | Ring | |
| 4,077,409 A * | 3/1978 | Murray et al. | 604/15 |
| 4,109,354 A | 8/1978 | Ronc | |
| 4,175,561 A | 11/1979 | Hirschman | |
| 4,276,881 A * | 7/1981 | Lilaonitkul | 604/14 |
| 4,291,696 A * | 9/1981 | Ring | 604/14 |
| 4,294,253 A | 10/1981 | Friese | |
| 4,305,391 A * | 12/1981 | Jackson | 604/366 |
| 4,328,804 A | 5/1982 | Shimatani | |
| 4,361,151 A | 11/1982 | Fitzgerald | |
| 4,405,323 A * | 9/1983 | Auerbach | 604/285 |
| 4,479,791 A * | 10/1984 | Sprague | 604/14 |
| 4,676,773 A * | 6/1987 | Sheldon | 604/16 |
| 4,726,805 A * | 2/1988 | Sanders, III | 604/15 |
| 4,755,166 A * | 7/1988 | Olmstead | 604/11 |
| 4,787,895 A * | 11/1988 | Stokes et al. | 604/358 |
| 4,816,100 A | 3/1989 | Friese | |
| 4,846,802 A * | 7/1989 | Sanders, III | 604/15 |
| 4,891,042 A * | 1/1990 | Melvin et al. | 604/18 |
| 4,911,687 A * | 3/1990 | Stewart et al. | 604/15 |
| 4,960,417 A * | 10/1990 | Tarr et al. | 604/15 |
| 5,165,152 A | 11/1992 | Kramer et al. | |
| 5,330,421 A | 7/1994 | Tarr et al. | |
| 5,346,468 A | 9/1994 | Campion et al. | |
| 5,374,258 A * | 12/1994 | Lloyd et al. | 604/358 |
| 5,403,300 A | 4/1995 | Howarth | |
| 5,445,605 A * | 8/1995 | Pluss | 604/13 |
| 5,531,674 A * | 7/1996 | Frayman | 604/11 |
| 5,542,914 A | 8/1996 | Van Iten | |
| 5,554,109 A * | 9/1996 | Frayman | 604/15 |
| 5,592,725 A * | 1/1997 | Brinker | 28/118 |
| 5,895,408 A | 4/1999 | Pagan | |
| 5,909,884 A | 6/1999 | Schwankhart | |
| 5,911,712 A * | 6/1999 | Leutwyler et al. | 604/379 |
| 6,177,608 B1 | 1/2001 | Weinstrauch | |
| 6,206,867 B1 | 3/2001 | Osborn et al. | |
| 6,310,269 B1 | 10/2001 | Friese et al. | |
| 6,358,235 B1 * | 3/2002 | Osborn et al. | 604/385.18 |
| 6,433,246 B1 * | 8/2002 | Nguyen et al. | 604/375 |
| 6,478,786 B1 | 11/2002 | Glaug et al. | |
| D485,354 S | 1/2004 | Carlin et al. | |
| 6,719,743 B1 | 4/2004 | Wada | |
| 6,748,634 B2 | 6/2004 | Nguyen et al. | |
| 6,755,808 B2 | 6/2004 | Balogh et al. | |
| 6,889,409 B2 * | 5/2005 | Friese et al. | 28/118 |
| 6,939,340 B1 * | 9/2005 | Berges | 604/385.17 |
| 6,953,456 B2 | 10/2005 | Fuchs et al. | |
| 7,059,026 B2 | 6/2006 | Friese et al. | |
| 7,070,585 B2 | 7/2006 | Jensen | |
| 7,087,045 B2 | 8/2006 | Jensen | |
| 7,338,483 B2 | 3/2008 | Carlin et al. | |
| 7,967,803 B2 | 6/2011 | Van Ingelgem et al. | |
| 2001/0014348 A1 | 8/2001 | Schoelling | |
| 2002/0151859 A1 * | 10/2002 | Schoelling | 604/385.17 |
| 2002/0157222 A1 | 10/2002 | Friese et al. | |
| 2003/0097108 A1 | 5/2003 | Hasse et al. | |
| 2003/0176844 A1 * | 9/2003 | Randall et al. | 604/385.17 |
| 2003/0176845 A1 * | 9/2003 | Kollwitz et al. | 604/385.17 |
| 2003/0208180 A1 | 11/2003 | Fuchs et al. | |
| 2004/0030316 A1 | 2/2004 | Gubernick et al. | |
| 2004/0199137 A1 * | 10/2004 | Lamb | 604/385.18 |
| 2005/0055001 A1 | 3/2005 | Cazzato et al. | |
| 2005/0113780 A1 | 5/2005 | Gatto et al. | |
| 2005/0113783 A1 | 5/2005 | Carlin et al. | |
| 2005/0113787 A1 | 5/2005 | Carlin | |
| 2005/0113788 A1 | 5/2005 | Carlin | |
| 2005/0113789 A1 * | 5/2005 | Jensen | 604/385.18 |
| 2005/0113807 A1 * | 5/2005 | Carlin | 604/904 |
| 2005/0143708 A1 * | 6/2005 | Hagberg et al. | 604/385.18 |
| 2005/0177090 A1 * | 8/2005 | Jensen | 604/14 |
| 2005/0193536 A1 * | 9/2005 | Ingelgem et al. | 28/118 |
| 2005/0256511 A1 | 11/2005 | Chase et al. | |
| 2005/0277904 A1 | 12/2005 | Chase et al. | |
| 2005/0283128 A1 | 12/2005 | Chase et al. | |
| 2006/0111662 A1 | 5/2006 | Karapasha et al. | |
| 2006/0167429 A1 * | 7/2006 | Denti et al. | 604/385.17 |
| 2006/0167430 A1 * | 7/2006 | Denti et al. | 604/385.17 |
| 2006/0241556 A1 | 10/2006 | Lochte et al. | |
| 2007/0083182 A1 * | 4/2007 | Schoelling | 604/385.18 |
| 2008/0154176 A1 * | 6/2008 | Van Ingelgem et al. | 604/18 |
| 2008/0195029 A1 | 8/2008 | Van Ingelgem et al. | |
| 2008/0200892 A1 * | 8/2008 | Van Ingelgem et al. | 604/379 |
| 2008/0221502 A1 | 9/2008 | Binner et al. | |
| 2009/0024103 A1 * | 1/2009 | Van Ingelgem et al. | 604/379 |
| 2009/0082712 A1 | 3/2009 | Hasse | |
| 2010/0121251 A1 | 5/2010 | Van Ingelgem et al. | |
| 2010/0318053 A1 | 12/2010 | Smet | |
| 2011/0201992 A1 | 8/2011 | Smet et al. | |
| 2011/0230854 A1 | 9/2011 | Smet | |
| 2011/0238028 A1 | 9/2011 | Smet | |
| 2012/0010587 A1 | 1/2012 | Smet | |
| 2012/0089111 A1 | 4/2012 | Magnusson et al. | |

FOREIGN PATENT DOCUMENTS

| | | |
|---|---|---|
| DE | 4 304 505 | 8/1994 |
| DE | 4 325 220 | 2/1995 |
| DE | 103 06 678 | 8/2004 |
| DE | 20320992 | 8/2005 |
| DE | 10 2005 030 182 | 1/2007 |
| DE | 10 2005 050514 | 4/2007 |
| EP | 0 355 396 | 2/1990 |
| EP | 0422 660 | 4/1991 |
| EP | 0639 363 | 2/1995 |
| EP | 0 692 233 | 1/1996 |
| EP | 1 027 874 | 8/2000 |
| EP | 1 108 408 | 6/2001 |
| EP | 1 208 827 | 5/2002 |
| EP | 1 481 656 | 5/2003 |
| EP | 1 459 720 | 9/2004 |
| EP | 1498093 | 1/2005 |
| EP | 1 547 554 | 6/2005 |
| EP | 1 547 555 | 6/2005 |
| EP | 1683503 | 7/2006 |
| EP | 1695 680 | 8/2006 |
| EP | 1704841 | 9/2006 |
| GB | 2120945 | 12/1983 |
| WO | WO 91/06272 | 5/1991 |
| WO | WO 96/27353 | 9/1996 |
| WO | WO 00/53141 | 9/2000 |
| WO | WO 02/49686 | 6/2002 |
| WO | WO 02/076357 | 10/2002 |
| WO | WO 02/078586 | 10/2002 |
| WO | WO 2005/063162 | 7/2005 |
| WO | WO 2007/088057 | 8/2007 |
| WO | WO 2009/129910 | 10/2009 |

OTHER PUBLICATIONS

European Search Report dated Jan. 20, 2011 from European patent Application No. EP 10169007.1.

Office Action dated Oct. 13, 2011 from U.S. Appl. No. 11/816,908, filed Aug. 22, 2007.

Search Report dated Jun. 4, 2004 from European Patent Application No. 03447303.

(56) References Cited

OTHER PUBLICATIONS

Search Report dated Apr. 11, 2006 from International Patent Application No. PCT/EP2006/000407.
Partial Search Report dated Aug. 17, 2005 from European Patent Application No. 05447004.
Search Report dated Nov. 10, 2005 from European Patent Application No. 05447065.
Search Report dated Apr. 28, 2006 from International Patent Application No. PCT/EP2006/001598.
Partial Search Report dated Nov. 14, 2005 from European Patent Application No. 05447042.
Search Report dated Jun. 29, 2007 from International Patent Application No. PCT/EP2007/000872.
Search Report dated Jun. 5, 2008 from International Patent Application No. PCT/EP2008/051418.
Office Action dated Jan. 23, 2007 from U.S. Appl. No. 11/021,671, filed Dec. 22, 2004.
Office Action dated Jul. 11, 2007 from U.S. Appl. No. 11/021,671, filed Dec. 22, 2004.
Office Action dated Mar. 6, 2008 from U.S. Appl. No. 11/021,671, filed Dec. 22, 2004.
Office Action dated Nov. 28, 2008 from U.S. Appl. No. 11/021,671, filed Dec. 22, 2004.
Office Action dated Jun. 24, 2009 from U.S. Appl. No. 11/021,671, filed Dec. 22, 2004.
Office Action dated Mar. 18, 2010 from U.S. Appl. No. 11/021,671, filed Dec. 22, 2004.
Office Action dated Sep. 21, 2010 from U.S. Appl. No. 11/813,970, filed Feb. 8, 2008.
Office Action dated Sep. 30, 2009 from U.S. Appl. No. 11/816,908, filed Aug. 22, 2007.
Office Action dated May 13, 2010 from U.S. Appl. No. 11/816,908, filed Aug. 22, 2007.
Office Action dated Sep. 22, 2010 from U.S. Appl. No. 12/278,228, filed Aug. 4, 2008.
International Search Report for International Application No. PCT/US2005/017884, mailed on Apr. 28, 2006.
International Search Report for International Application No. PCT/EP2011/061435, mailed on Aug. 9, 2011.
Final Office Action for U.S. Appl. No. 11/813,970 dated Mar. 17, 2011.
Final Office Action for U.S. Appl. No. 12/278,228 dated Mar. 22, 2011.
International Search Report for International application No. PCT/EP2009/067047, dated Feb. 17, 2010 by European Patent Office.
International Search Report for International application No. PCT/EP2009/065089, dated Jun. 9, 2010 by European Patent Office.
International Search Report for International application No. PCT/EP2009/063998, dated Mar. 11, 2010 by European Patent Office.

\* cited by examiner

TAMPON APPLICATOR ASSEMBLY

RELATED APPLICATIONS

This application is the U.S. National Phase under 35 U.S.C. §371 of International Application PCT/EP2006/002075, filed Mar. 7, 2006, which claims priority to EP 05447065.3, filed Mar. 25, 2005.

FIELD OF THE INVENTION

This invention relates to tampon applicator assemblies and is particularly directed toward such assemblies provided in a compact, unobtrusive, conveniently short form.

BACKGROUND OF THE INVENTION

Most commercially available assemblies for introducing catamenial tampons intravaginally comprise a tampon disposed inside a tampon applicator consisting of a pair of telescoping tubes.

In assemblies comprising a non-compact tampon applicator, a tampon is disposed in an outer tube which is combined with an ejector tube adapted to slideably expel the tampon from the outer tube. The ejector tube is smaller in diameter than the outer tube and is telescopically positioned therein so that by moving the ejector tube into one end of the outer tube, the tampon may be ejected from the opposite end. The outer tube is, of necessity, longer than the tampon and, to insure complete ejection of the tampon from the outer tube, generally the ejector tube is likewise longer than the outer tube. Consequently, the overall length of such assemblies is always more than twice the length of the tampon. Reducing the size of the assemblies and of the corresponding commercial packages provided an incentive to develop the compact tampon applicators.

In assemblies comprising a compact tampon applicator, the ejector tube is telescoped completely or almost completely into the outer tube while the tampon is stored in the distal end of the ejector tube. Operatively, the ejector tube is "cocked" by being withdrawn proximally most of the way from its stored position in the outer tube (leaving behind the tampon) until the distal end of the ejector tube is positioned to engage the proximal end of the stored tampon. In a subsequent ejection step, the ejector tube is reciprocated back into the outer tube, thereby expelling the tampon from the opposite end of the outer tube.

To prevent displacement of the tampon together with the ejector tube during the cocking step, the outer tube typically includes a means to engage the distal end of the tampon. Nevertheless, when the ejector tube is being withdrawn, the close association between the outer surface of the tampon and the opposing inner surface of the ejector tube may occasionally override this engagement, leading to displacement of the tampon. Because the hygienic requirements preclude further manipulation of the assembly by the user to reposition the tampon, assemblies with displaced tampons are unusable and need to be discarded. Hence, a small proportion of presently existing assemblies malfunctions and must be discarded, which may lead to consumer annoyance especially in situations when no other assemblies are at hand.

Further, the ejector tube of compact tampon applicators usually includes inwardly flexible distal fingers. When the ejector tube is being withdrawn, these fingers push against the outer surface of the tampon. Therefore, the surface or the edges of these fingers may occasionally scrape material from the outer surface of the tampon, leading to undesirable loss of material. Moreover, the outer tube of compact tampon applicators similarly includes inwardly flexible distal petal sections. These petal sections press against the outer surface of the tampon when this is being ejected from the applicator. Hence, the surface or edges of the petal sections may also retain material from the outer surface of the tampon, leading to further unwanted loss of material.

The present invention addresses the above problems of displacement of the tampon during the cocking step and of loss of tampon material during the cocking and ejection steps in assemblies comprising compact tampon applicators.

SUMMARY OF THE INVENTION

In an aspect, the present invention provides a novel assembly which comprises: a compact tampon applicator and a tampon having a longitudinal body defining an insertion end, a withdrawal end, a central section extending there between, a longitudinal axis, and an outer surface, characterised in that said outer surface of the tampon comprises at least one area of radial depression.

Such areas of radial depression are defined by a smaller radius on transverse cross-section than adjacent areas of the outer surface of the tampon and therefore will be radially spaced away from the structures of the applicator which may contact the outer surface of the tampon during use of the assembly, i.e., during cocking and ejection steps. Such structures may particularly include the inner surface of the ejector tube and the surface and edges of the fingers of the ejector tube and of the petal sections of the outer tube. Consequently, the areas of radial depression will not contact the respective structures of the applicator during use of the assembly. This will reduce the total amount of contact between the outer surface of the tampon and the respective structures of the applicator during use. Reduction of contact between the outer surface of the tampon and the inner surface and fingers of the ejector tube may decrease the overall friction and therefore advantageously minimizes the likelihood of displacement of the tampon in the proximal direction during the cocking step, and facilitates easier withdrawal of the ejector tube during the cocking step. Further, reduction of contact between the outer surface of the tampon and the inner surface and/or edges of the fingers and of the petal sections may decrease the overall friction and therefore advantageously minimize disruption of the tampon surface by said structures and loss of tampon material displaced by said fingers or petal sections during cocking and ejection steps.

In a particularly advantageous embodiment, said tampon may comprise at least one radially pressed groove.

DETAILED DESCRIPTION OF THE INVENTION

Figure 1:
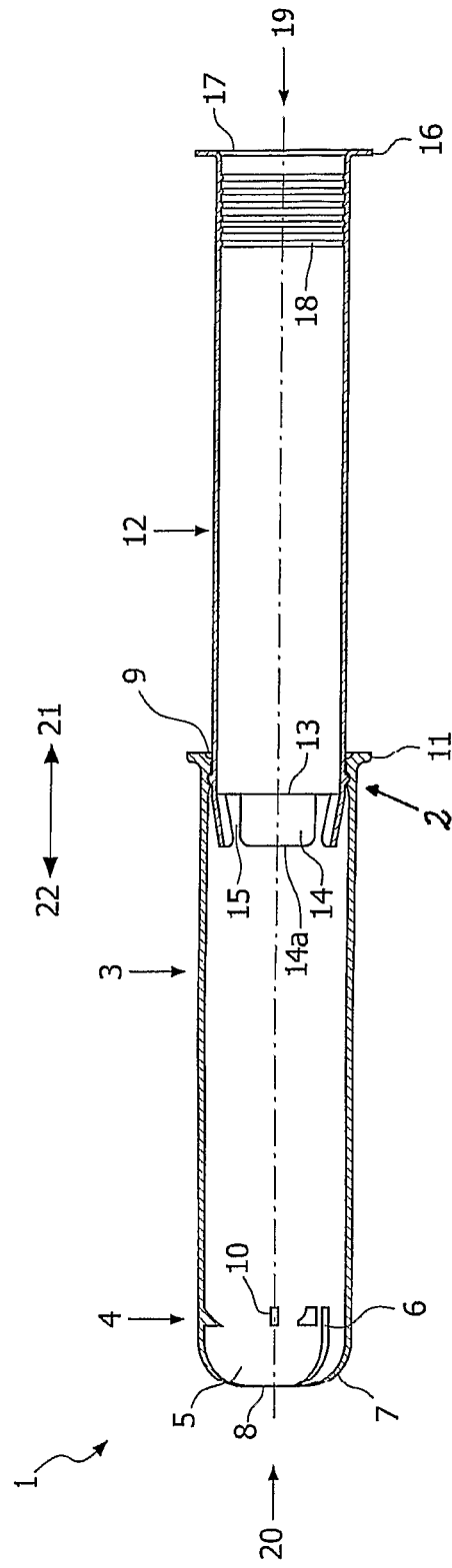
FIG. 1 illustrates a side view of an exemplary embodiment of a compact tampon applicator suitable for use in the assembly of the present invention. The applicator is in cocked position, i.e., the ejector tube 12 is withdrawn out most of the way from the outer tube 3.

The invention is further explained with reference to FIGS. 1 to 4, which illustrate preferred, but non-limiting embodiments of the present assembly and of its parts, i.e., a compact tampon applicator 1 and a tampon 23.

The present assembly defines a proximal end 19 and a distal end 20. As used herein, the term "proximal end" 19 refers to those portions of the assembly and of its parts that are most remote from the body of a user when the tampon 23 is being emplaced within a body cavity, e.g., a vaginal cavity. The term "distal end" 20 refers to those portions of the assembly and of its parts that are closest to the body of a user when the tampon is being emplaced. Accordingly, the terms "proximal" or "proximally", and "distal" or "distally", as used herein, specify that a given portion or structure of the assembly or of its parts is relatively closer to, respectively, the proximal end 19 or the distal end 20 of the assembly or of its parts. Similarly, the terms "proximal direction" 21 or "distal direction" 22 refer to the directions towards the proximal end 19 or towards the distal end 20 of the assembly or of its parts, respectively.

As disclosed herein, the term "compact tampon applicator" refers to a tampon applicator 1 comprising an ejector tube 12 adapted to store a tampon 23 therein and an outer tube 3 dimensioned to fit closely and telescopically over the ejector tube 12. The outer tube 3 is configured to pass the tampon 23 through an opening 8 in its distal end 4 during an ejection operation. When an assembly comprising a compact tampon applicator 1 and a tampon 23 is prepared for use by a consumer, the tampon 23 is stored in the distal end 13 of the ejector tube 12 and the ejector tube 12 is telescoped completely or almost completely into the outer tube 3. Operatively, the ejector tube 12 is cocked by being withdrawn in the proximal direction 21 most of the way from its stored position in the outer tube 3, while the tampon 23 is left behind in the distal end 4 of the outer tube 3, until the distal end 13 of the ejector tube 12 is positioned to engage the proximal end 24 of the stored tampon 23. Accordingly, compact tampon applicators typically include a means 10 for securing the stored tampon 23 in the distal end 4 of the outer tube 3 to prevent its displacement in the proximal direction 21 during the withdrawal of the ejector tube 12 from the outer tube 3. Further, compact tampon applicators 1 usually include a restraining means 2, e.g., an interlocking restraining means, to prevent disassembly of the outer 3 and ejector 12 tubes during the cocking step. After the ejector tube 12 has been cocked, it is reciprocated in the distal direction 22 back into the outer tube 3, thereby expelling the tampon 23 from the distal end 4 of the outer tube 3.

The cylindrical outer tube 3 has at its distal end 4 a plurality, i.e., 2 or more, e.g., 2 to 15, preferably 2 to 8, more preferably 2 to 6, and most preferably 4, of conventional petal sections 5 which are separated from each other by respective slots 6. The petal sections 5 are made relatively flexible and are normally biased in a substantially arcuate closed configuration to form a rounded tip 7 having a central opening 8 at the distal end 4. This rounded shape of the distal end 4 helps facilitate the insertion of the applicator 1 into the vaginal cavity. Such outer tubes 3 are preferably constructed from any suitable smooth plastic material, e.g., polyethylene, and may be, e.g., molded (e.g., injection molded) or prepared from extruded tubing. The opposite or proximal end 9 of the outer tube 3 is open.

The outer tube 3 of the applicator 1 further includes a plurality, i.e., 2 or more, e.g., 2 to 15, preferably 2 to 8, more preferably 2 to 6, and most preferably 4 inward projections 10 formed along the inner circumference adjacent to the proximal end of the petal sections 5. For example, one or more such inward projection 10 may be disposed approximately at the base of each respective petal section 5. The inward projections 10 serve to engage the insertion end 35 of a tampon 23 which may be stored in the distal end 13 of an ejector tube 12, thereby preventing axial movement of the tampon in the proximal direction 21 during the cocking of the ejector tube 12. Therefore, the inward projections 10 are often inclined towards the distal end 4, such as to securely grip a tampon 23 and prevent its movement in the proximal direction (similar to the way a speed nut functions, making a unidirectional jamming engagement). These projections 10 may have various shapes known in the art, e.g., they may be flaps disposed in an inward direction generally perpendicular to the axis of the outer tube 3 and preferably canted towards the distal discharge end 4 thereof. In FIGS. 1 and 3 the projections 10 have a substantially right triangular profile with the hypotenuse (i.e., the longest side) extending at an acute angle from the inner wall of the outer tube 3 towards the central opening 8, one of the catheti (i.e., the shorter sides) facing the distal end 4 of the outer tube 3, and the other cathetus being the contact side with the inner surface of the outer tube 3. The projections may be relatively thin in the circumferential direction, with thickness ranging, e.g., from 0.2 mm to 5 mm, which may save raw material. Alternatively, a continuous circumferential ring may be provided instead of a plurality of inward projections 10.

The outer tube 3 of the present applicator 1 may further comprise an outwardly directed circumferential flange 11 at its proximal end 9. The outer proximal surface of the outer tube 3 may optionally be provided with a ridged or knurled surface, which provides for a firmer grip when this portion of the outer tube 3 is held between fingers.

The cylindrical ejector (or inner) tube 12 serves as a hollow plunger for ejecting a tampon 23 positioned within the distal end 4 of the outer tube 3. Ejector tube 12 may be constructed from any suitable smooth plastic material, e.g., polyethylene, and may be, e.g., molded (e.g., injection molded) or prepared from extruded tubing. The ejector tube 12 is dimensioned to easily slide within the outer tube 3, with minimal clearance in between. The ejector tube 12 is also preferably slightly longer that the outer tube 3 to assure complete ejection and proper depth of placement of the tampon 23. Being hollow, the ejector tube also permits proper placement of a withdrawal string 26 usually attached to the withdrawal end 24 of the tampon. The distal end 13 of the ejector tube 12 is typically formed with a plurality, i.e., 2 or more, e.g., 2 to 15, preferably 2 to 8, more preferably 2 to 6, and most preferably 4, of fingers 14 which are separated from each other by slots or openings 15, through which the inward projections 10 of the outer tube 3 may extend to engage the tampon 23 disposed therein. In the same manner as with petal sections 5 of the outer tube 3, the fingers 14 are made so as to be slightly biased towards a closed configuration. Such fingers 14 tend to be considerably shorter than the petal sections 5 of the outer tube 3, e.g., to give a stronger structure. The ejector tube 12 may be functional also without such fingers 14 if a tampon is sufficiently expansive to fit closely within the outer tube 3 to ensure positive engagement by an unmodified distal end 13 of the ejector tube 12 against the withdrawal end 24 of the tampon 23 during the ejection step.

The ejector tube 12 also includes an outwardly directed circumferential retention flange 16 at its proximal end 17. The flange 16 controls the extent of insertion of the ejector tube 12 into the outer tube 3 of the applicator 1. The flange 16 of the ejector tube 12 will abut the retention flange 11 of the outer tube 3 when the ejector tube 12 is fully inserted into the outer tube 3. The inner proximal portion of the ejector tube 12 may optionally be provided with a ridged or knurled surface 18, which provides for a firmer grip when a finger is inserted into the ejector tube.

The compact tampon applicator 1 of the present assembly further comprises a restraining means 2 to prevent disassembly of the outer 3 and ejector 12 tubes when the ejector tube 12 is partially withdrawn from the outer tube 3 during the cocking step. Typically, the restraining means is formed by circumferentially extending, raised structures provided on the outer distal surface of the ejector tube 12 and on the inner proximal surface of the outer tube 3. These structures may be, e.g., rings, ribs or protrusions.

For example, a stopping ring may project radially inwardly from the inner surface of the outer tube 3 near its proximal end 9 and another ring or a plurality of circumferentially aligned protrusions may project radially outwardly from the outer surface of the ejector tube 12 near its distal end 13. The height of these structures is such that they are radially spaced from the opposing surface of the tube 3,12 other than that on which they are provided when the ejector tube 12 is inserted in the outer tube 3 and when it is being withdrawn in the proximal direction most of the way. However, the structures overlap radially, and will eventually engage when the ejector tube 12 is sufficiently withdrawn from the outer tube 3, thus preventing complete withdrawal and disassembly of the applicator 1.

Essentially any restraining means known in the art may be used in the compact tampon applicator of the present assembly. For example, these encompass any of the restraining means described in EP 0 355 396 B1 on page 9, line 1, through page 11, line 31 under the heading "Earlier Tube Interlocks", which are herein incorporated by reference. Further, these also encompass the restraining means disclosed in EP 0 355 396 B1, in particular on page 8, line 1 through line 57 under the heading "Improved Tube Interlock", herein incorporated by reference, which comprised a pair of two raised rings on the inner surface of the outer tube 3 at its proximal end 9, the respective facing slopes of which defined an interposed valley, and another raised ring-like structure on the outer distal surface of the ejector tube 12. When the ejector tube 12 was withdrawn from the outer tube 3 in the proximal direction 21, the ring-like structure on the ejector tube 12 became engaged (i.e., interlocked) within the valley on the outer tube 3, which prevented the disassembly of the outer and ejector tubes. In interlocked position, all surfaces of the ring-like structure on the ejector tube 12 were closely engaged with the respective facing surfaces of the valley on the outer tube 3. This advantageously restricted lateral movement (wobble) of the ejector tube 12 relative to the outer tube 3 in the interlocked position, which further decreased the chance of disassembly. Yet further, these also encompass the restraining means disclosed in an earlier filed, not yet public patent application EP 05447042.2 (herein incorporated by reference and illustrated in FIGS. 1 and 3A), which comprised a circumferentially-extending raised means 2a typically provided on the outer distal surface of the ejector tube 12 and a set of at least three adjacent circumferentially-extending raised rings 2b,2c,2d typically provided on the inner proximal surface of the outer tube 3. Two of the raised rings 2b,2c defined an interposed valley which could engage with the raised means 2a with a degree of freedom, while the additional at least one ring 2d provided an extra means of restricting the lateral movement or wobble of the ejector tube 12 relative to the outer tube 3. The presence of the additional ring 2d advantageously eliminated the requirement (present in the restraining means of EP 0 355 396 B1) for exact complementarity between the surfaces of the valley formed by the two other raised rings 2b,2c and the surfaces of the raised means 2a.

Figure 3A:
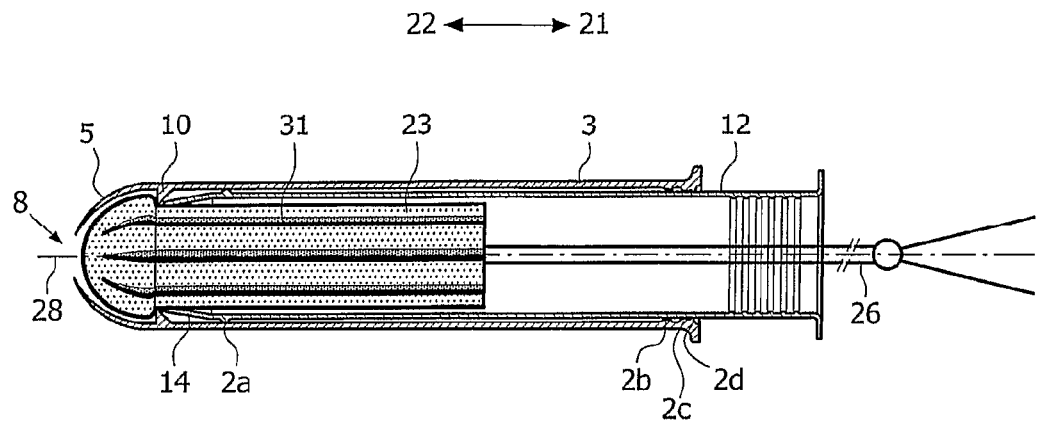
FIG. 3A illustrates a side view of an exemplary embodiment of the assembly of the present invention. The applicator is shown in a longitudinal cross section.
Figure 3B:
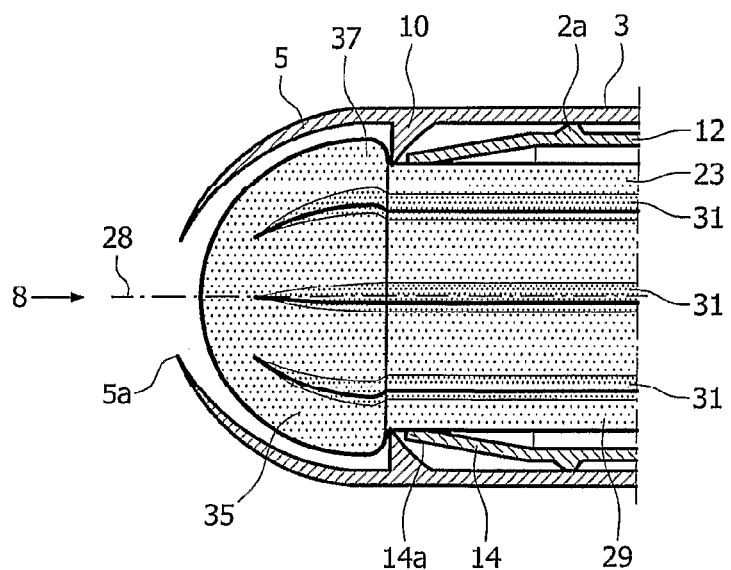
FIG. 3B illustrates a detail of the distal end of the assembly in FIG. 3A.
Figure 4:
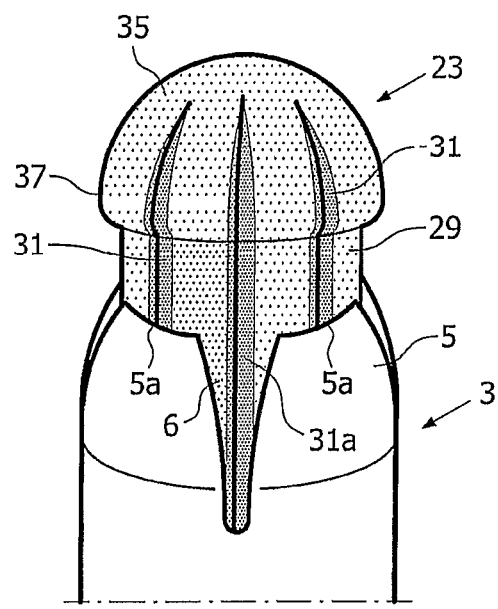
FIG. 4 illustrates a front top view of a tampon partially ejected from the outer tube 3.

When the present assembly of a compact tampon applicator 1 and a tampon 23 is prepared for use, the ejector tube 12 is disposed within the outer tube 3 and over a stored tampon 23 (as shown in FIGS. 3A and 3B). The distal ends 13 or the fingers 14 of the ejector tube 12 may abut the inward projections 10 or the inward projections 10 of the outer tube 3 may also project through the slots 15 separating the fingers 14 of the ejector tube 12 to engage the tampon 23. The flexible fingers 14 of the ejector tube 12 may be biased flexibly outward by the carried tampon 23. This permits the fingers 14, and the remainder of the ejector tube 12, to pass over the tampon 23 that is secured in the outer tube 3 by the inward projections 10 during partial withdrawal of the ejector tube 12. Then, because of the stiff flexibility of the fingers 14, when the ejector tube 12 is sufficiently withdrawn, the fingers 14 will flex inwardly to a lesser diameter than that of the tampon. Consequently, when the ejector tube 12 is axially moved in the distal direction 22, the tampon will be engaged at its proximal end 24 by the fingers 14 and urged out the distal discharge end 4 of the outer tube 3.

Any compact tampon applicator 1 known in the art of the type essentially as described above is suitable for use in the assembly of the present invention.

It is an object of the present invention to provide an improved assembly comprising a compact tampon applicator 1 and a tampon 23. The assembly of the present invention provides for reduced disruption of the tampon surface and reduced loss of tampon material during the cocking and ejection steps, as well as for easier withdrawal of the ejector tube 12 and decreased likelihood of tampon displacement during the cocking step. The present invention achieves these advantages by providing an assembly comprising a tampon 23 having its outer surface 29 modified such as to reduce the total amount of contact and/or friction between said outer surface 29 of the tampon 23 and structures of the applicator 1 during use of the assembly.

Accordingly, in an aspect the present invention provides an assembly comprising:
  a compact tampon applicator 1, and
  a tampon 23 having a longitudinal body defining an insertion end 35, a withdrawal end 24, a central section 27 extending there between, a longitudinal axis 28, and an outer surface 29,
characterised in that said outer surface 29 of the tampon 23 comprises at least one area of radial depression.

A tampon 23 according to the present invention has a longitudinal body which defines a distal insertion end 35, a proximal withdrawal end 24, and a central section 27 extending there between. The tampon further defines a longitudinal axis 28 and an outer surface 29. The tampon 23 or at least the central section 27 of the tampon 23 may have an essentially cylindrical shape, meaning that of simple geometrical forms a cylindrical envelope may most closely approximate the overall shape of the tampon 23 or at least of its central section 27.

As used herein, the term "outer surface" 29 of the tampon mainly refers to the surface defined by the central section 27 of the tampon 23. The term "outer surface" 29 encompasses the entire surface of the tampon 23 or more specifically of its central section 27, regardless of the radial distance of said surface from the longitudinal axis 28. Hence, "outer surface" 29 includes both the surface defined by areas of radial depression (e.g., grooves 31) and the surface defined by regions adjacent to such areas (e.g., ribs 32).

Prior art assemblies comprised tampons having an essentially cylindrical shape with an even outer surface. Hence, circumferences of transverse cross-sections through the outer surface of such tampons were circular or substantially circular. A "circular" circumference is one defined by a centre and a uniform radius. While deviations from circular circumference may have occurred in these tampons, such deviations were mostly limited and occurred, e.g., due to the nature of the material of the tampons or due to imperfections in manufacturing, rather than due to a purposeful design.

In contrast to prior art assemblies, it is an aspect of the present invention that the outer surface 29 of the tampon 23 comprises at least one area of radial depression. An "area of radial depression" refers to an area on the outer surface 29 of the tampon 23 which is radially closer to the longitudinal axis 28 than the outer surface 29 adjacent to said area. Hence, in a transverse cross-section through a region of the outer surface 29 of the tampon 23 comprising an area of radial depression, said area will be defined by a smaller radius than the adjacent outer surface 29. The tampon 23 will have a smaller diameter in transverse cross-section at such area of radial depression.

Thus, the outer surface 29 of the tampon 23 of the present assembly will comprise one or more areas of radial depression which are radially closer to the longitudinal axis 28 than the adjacent outer surface 29. These areas will be radially spaced away from the structures of the applicator 1 which may contact the outer surface 29 of the tampon 23 during use of the assembly. Such structures in particular include the inner surface of the ejector tube 12 and the inner surface and distal and/or lateral edges of the fingers 14 of the ejector tube 12 during the cocking step, and the inner surface and distal and/or lateral edges of the petal sections 5 of the outer tube 3 during the ejection step. Consequently, the areas of radial depression on the outer surface 29 of the tampon 23 will not contact the respective structures of the applicator 1 during use of the assembly. Rather, only the circumferential surface of regions adjacent to the areas of radial depression will contact the respective structures of the applicator 1 during use of the assembly.

This will reduce the total amount of contact between the outer surface 29 of the tampon 23 and the respective structures of the applicator 1 during use of the assembly. Reduction of contact between the outer surface 29 of the tampon 23 and the inner surface and fingers of the ejector tube 12 decreases the overall friction between these elements and therefore advantageously minimizes the likelihood of displacement of the tampon 23 in the proximal direction 21 during the cocking step. Moreover, it also facilitates easier withdrawal of the ejector tube 12 during the cocking step. Further, reduction of contact between the outer surface 29 of the tampon 23 and the inner surface and/or edges of the fingers 14 and of the petal sections 15 decreases the overall friction and therefore advantageously minimizes disruption of the tampon surface by said structures and loss of tampon material displaced by said fingers 14 or petal sections 5 during cocking and ejection steps.

The tampon may comprise between 1 and 50 areas of radial depression, preferably between 2 and 20, and more preferably between 4 and 12 such areas. Exemplary tampons may comprise 1, 2, 3, 4, 5, 6, 7, 8, 9, 10, 11, or 12 such areas.

The proportion of the outer surface 29 of the tampon 23 defined by such areas of radial depression may be at least 1%, or at least 5%, or at least 10%, or at least 20%, or at least 30%, or at least 40%, or at least 50%, and up to 95%, or up to 80%, or up to 70%, or up to 60% of the total outer surface 29 of the tampon 23, including ranges defined by a combination of any lower and higher limits listed above.

The depth of an area of radial depression is maximal where the radius in transverse cross-section is minimal. The maximum depth of such areas may range between 0.2 and 10 mm, preferably between 0.5 mm and 8 mm, more preferably between 1 mm and 6 mm, and even more preferably between 2 mm and 6 mm.

The contact between the outer surface 29 of the tampon 23 and the respective structures of the applicator 1 during use of the assembly may be reduced, e.g., by at least 5%, preferably at least 10%, more preferably at least 20%, and most preferably at least 30% compared to prior art assemblies having tampons without areas of radial depression.

The proportion of outer surface 29 of the present tampon 23 which at any time during use of the assembly will come in contact with any of the respective structures of the applicator 1 may be less than 95%, preferably less than 90%, more preferably less than 80%, and most preferably less 70% of the total outer surface 29 of the tampon 23.

In an embodiment, the at least one area of radial depression on the outer surface 29 of the present tampon 23 may be a radially pressed groove 31. A groove 31 represents a distinct area of radial depression on the outer surface 29 of the tampon 23 which may be at least in part defined by its length, width, depth and orientation. Typically, the length of a groove 31 is greater than its width.

Accordingly, the present invention also provides an assembly comprising:
  a compact tampon applicator 1, and
  a tampon 23 having a longitudinal body defining an insertion end 35, a withdrawal end 24, a central section extending there between 27, a longitudinal axis 28, and an outer surface 29,
characterised in that said outer surface 29 of the tampon 23 comprises at least one radially pressed groove 31.

Hence, in a transverse cross-section through a region of the outer surface 29 of the tampon 23 comprising a groove 31 (see FIG. 2B), said groove is defined by a smaller radius than the adjacent outer surface 29. The tampon 23 will have a smaller diameter at such groove 31. Hence, the outer surface 29 of the tampon 23 defined by a groove 31 will be radially spaced away from the respective structures of the applicator 1 which may contact the outer surface 29 of the tampon 23 during use of the assembly and will therefore not contact these structures. Therefore, provision of grooves 31 on the outer surface 29 of the tampon 23 will reduce the total contact between the outer surface 29 of the tampon 23 and the respective structures of the applicator 1 during use of the assembly, thus reducing the overall friction and advantageously decreasing the likelihood of tampon displacement during the cocking step, facilitating easier withdrawal of the ejector tube 12 during the cocking step, and reducing the disruption of the outer surface 29 of the tampon and 23 loss of tampon material during the cocking and ejection steps.

In an embodiment, the tampon comprises at least 1 groove 31. In another embodiment, the tampon comprises at least 3 grooves 31. For example, the tampon 23 may comprise between 1 and 50 grooves 31, preferably between 2 and 20, more preferably between 4 and 12 and most preferably about 8 grooves 31. Exemplary tampons may comprise 1, 2, 3, 4, 5, 6, 7, 8, 9, 10, 11, or 12 grooves. The tampon 23 may have an even or odd number of grooves 31. An even number may be preferred due to manufacturing requirements.

The proportion of the outer surface 29 defined by the grooves 31 may be at least 1%, or at least 5%, or at least 10%, or at least 20%, or at least 30%, or at least 40%, or at least 50%, and up to 95%, or up to 80%, or up to 70%, or up to 60% of the total outer surface 29 of the tampon 23, including any ranges defined by a combination of any lower and higher limits listed above.

The depth a groove 31 is maximal where the radius in transverse cross-section is minimal. The maximum depth of grooves 31 may range between 0.2 and 10 mm, preferably between 0.5 mm and 8 mm, more preferably between 1 mm and 6 mm, and even more preferably between 2 mm and 6 mm.

The circumferential width of grooves 31 may range, e.g., from 0.1 mm to 1 cm, preferably from 0.2 mm to 5 mm, more preferably from 0.5 mm to 2 mm.

In an embodiment, grooves 31 may be longitudinal, i.e., extending along at least a portion of the length of the outer surface 29 of the tampon 23. In the broadest meaning, a longitudinal groove 31 may be any which, in the direction of its length, is not perpendicular to the longitudinal axis 28 of the tampon 23. A longitudinal orientation of grooves 31 may be advantageous, because such grooves 31 may decrease the outer surface 29 of the tampon 23 capable of contacting the respective structures of the applicator 1 along a given length of the tampon 23.

In an embodiment, grooves 31 may be parallel to the longitudinal axis 28 of the tampon. Hence, such grooves 31 will be oriented essentially in the direction of the movement of the ejector tube 12 during the cocking step and of the tampon 23 during the ejection step. Such grooves 31 may therefore homogeneously reduce the outer surface 29 of the tampon 23 capable of contacting the respective structures of the applicator 1 along a given length of the tampon.

In a further embodiment, longitudinal grooves 31 may be spirally or helically shaped in the axial direction. Such grooves 31 are longer than grooves 31 parallel to the longitudinal axis and therefore will further reduce the outer surface 29 of the tampon 23 capable of contacting the respective structures of the applicator 1 during use. Moreover, such grooves 31 will cover a greater circumferential area of the outer surface 29 of the tampon 23. This reduces the chance (which may exist with grooves parallel to the longitudinal axis, as exemplified by groove 31a in FIG. 4) that a groove would be aligned with the slots 15,6 separating the fingers 14 or petal sections 15 and would therefore not contribute to reducing the contact between the outer surface 29 of the tampon 23 and the fingers 14 or petal sections 5 of the applicator 1 during use of the assembly. With spirally or helically shaped grooves 31, even when a particular groove 31 is aligned with the slots 15,6 in one position of the assembly, it will become aligned with the fingers 14 or petal sections 15 when the ejector tube 12 is being withdrawn or when the tampon 23 is being ejected during use.

Spirally or helically shaped grooves 31 may extend over various portions of the tampon circumference. For example, such grooves 31 may extend over at least about 10°, 20°, 30°, 40°, 50°, 60°, 70°, 80°, 90°, 100°, 120°, 130°, 140°, 150° or over more than 150° of the tampon circumference, e.g., over 80° to 120°, or 80° to 150°.

In a preferred embodiment, longitudinal grooves 31 extend between the insertion end 35 and the withdrawal end 24 of the tampon. This means that such grooves 31 will extend along the entire length of the tampon 23 or of its central portion 27. This will advantageously reduce the total contact between the outer surface 29 of the tampon 23 and the respective structures of the applicator 1 along the entire length of the tampon 23 or of its central portion 27 during use of the assembly.

In a preferred embodiment, when the outer surface 29 of the tampon 23 comprises two or more longitudinal grooves 31, these may be spaced circumferentially at regular intervals, i.e., at regular circumferential angle intervals. This will advantageously reduce the total contact between the outer surface 29 of the tampon 23 and the respective structures of the applicator 1 equally around the circumference of the tampon 23 during use of the assembly.

Preferably, the distal edges 14a of the fingers 14 of the ejector tube 12 and the distal edges 5a of the petal sections 5 of the outer tube 3 will be longer than the width of the longitudinal grooves 31, such that these edges 14a,5a are not capable of entering the grooves 31 and making contact with the surface within the grooves 31. The width and number of the grooves 31 and the size and number of fingers 14 and petal sections 5 may be selected such that during use of the assembly, the surface and lateral and/or distal edges of the fingers 14 and petal sections 5 will contact a surface of the tampon which comprises at least one groove 31. This will minimize the contact between said fingers 14 and petal sections and the outer surface 29 of the tampon 23.

Preferably, the orientation of the tampon 23 in the assembly will be such that the projections 10 of the outer tube 3 do not become located within the grooves 31, as this would compromise the engagement between the projections 10 and the distal portion of the tampon 23. To avoid orientation problems, e.g., the number of protrusions 10 may be at least one more than the number of grooves 31, or the grooves 31 may be spiral or helical, or the thickness of the inward projections 10 in the circumferential direction may be greater than the width of the grooves 31 of the tampon 23.

It is to be understood that an area of radial depression on the outer surface 29 of the tampon 23, e.g., a groove 31, also defines adjacent regions of the outer surface 29 having a greater radius in transverse cross-section. For example, a groove 31 may define two adjacent ribs 32 which are radially relatively more protruding than said groove 31. Similarly, two nearby grooves 31, e.g., grooves parallel to each other, define a radially relatively more protruding rib 32 in between.

The circumferential surface of such radially relatively more protruding regions (i.e., relative to areas of radial depression) of the outer surface 29 will define the maximum outer diameter 30 of the tampon in transverse cross-section. For example, if the outer surface 29 of the tampon 23 is provided with radially pressed longitudinal grooves 31, said grooves 31 define adjacent longitudinal ribs 32 and the circumferential surface of the ribs 32 defines the maximum outer diameter 30 of the tampon 23 or of its central section 27 in transverse cross-section. Such maximum outer diameter 30 of the tampon 23 or of its central section 27 may typically range from 5 mm to 25 mm, preferably from 8 mm to 18 mm, more preferably from 10 mm to 16 mm. The circumferential surface of the ribs 32 will contact the respective structures of the applicator 1 during use of the assembly.

Preferably, the maximum outer diameter 30 of the tampon 23 approximates the inner diameter of the ejector tube 12, such that a contact is obtained between at least a portion of the outer surface 29 of the tampon 23 and the inner surface of the ejector tube 12. This contact helps to maintain proper positioning of the tampon 23 within the ejector tube 12. In general, the inner surface of the ejector tube 12 which is configured for contacting the tampon is flat, i.e., essentially without distinct protrusions or depressions.

The maximum outer diameter 30 of the tampon 23 or of its central portion 27 may be essentially uniform in the longitudinal direction, or it may vary. For example, the portion of the tampon close to the withdrawal end 24 may have a greater maximum outer diameter 30 than the remainder of the central section 27. Such proximal thickening of the tampon 23 may decrease the risk of leakage of body fluids when the tampon 23 is placed in the vagina. When the maximum outer diameter 30 of the tampon 23 or of its central section 27 varies in the longitudinal direction, the change may be gradual.

In an embodiment, the density of absorbent material may be essentially the same across the transverse cross-section of the tampon 23.

In another embodiment, the tampon 23 may comprise a central core 33 of highly compressed absorbent fibrous material from which longitudinal ribs 32 extend radially outward. In an embodiment, the longitudinal ribs 32 may be at least partially relatively uncompressed compared with said core 33. The diameter of said core in transverse cross-section may be, e.g., up to 5 mm.

Accordingly, in a non-limiting example, a tampon 23 suitable for the present assembly may have a compressed, central, generally cylindrical fibre core 33 of highly compressed fibrous material and further comprise longitudinal ribs 32 extending radially outward from said core 33 and separated by longitudinal grooves 31 in between. The longitudinal grooves 31 and ribs 32 may be parallel to the longitudinal axis (i.e., straight), or may extend spirally or helically in the axial direction. They may also have other shapes, e.g., extend sinusoidally in the axial direction. The longitudinal ribs 32 may be at least partially relatively uncompressed compared with the fibre core 33, and may preferably have, in particular close to their circumferential surface, a soft fibrous structure. The longitudinal ribs 32 may extend outward at equal circumferential angle intervals from the fibre core 33 between the insertion end 35 and the withdrawal end 24 of the tampon 23. Besides reducing the outer surface 29 of the tampon 23 coming into contact with the respective structures of the applicator 1 during use of the assembly, provision of grooves 31 also enlarges the total outer surface 29 of the tampon 23 compared to a tampon with an even cylindrical outer surface without any areas of radial depression, such as grooves 31. This may advantageously increase the absorption capacity and expansion capacity of the tampon 23, and thereby reduce risk of leakage. A tampon 23 of the present invention may preferably expand widthwise (i.e., assume an increased diameter in transverse cross-section) upon absorption of fluid, e.g., menstrual fluid. Provision of longitudinal grooves 31 defining longitudinal ribs 32 may facilitate such widthwise expansion, as is known in the art.

The areas of radial depression may be introduced to the outer surface 29 of the tampon 23 by any method known in the art, e.g., by a pressing step. For example, processes to provide an essentially cylindrical tampon blank with grooves 31, e.g., longitudinal grooves 31, are well known in the art. Such processes and apparatuses for use in these processes are disclosed, e.g., in WO 02/078586, EP 0 422 660, US 2002/0157222, U.S. Pat. No. 5,592,725, U.S. Pat. No. 5,895,408, EP 1 108 408, US 2003/0208180, WO 00/53141 and EP 0 639 363, which are hereby incorporated by reference.

In general, such processes involve several steps. First, an essentially cylindrical tampon blank having a circumferential surface is provided, said tampon blank usually formed by rolling up a length of a continuous fibrous web. Next, said tampon blank is inserted in a press comprising press jaws which include penetrating segments and pressing shoulders and the tampon blank is simultaneously pressed in the press jaws at strip shaped sections of the circumferential surface, wherein the penetrating segments penetrate the cylindrical blank to form grooves 31 defining the ribs 32 and the pressing shoulders press on the circumferential surface of the resulting ribs 32. The radial length of the penetrating segments determines the depth of the grooves 31, the thickness of the penetrating segments controls the width of the grooves 31 and the shape of the penetrating segments controls the shape of the grooves 31 in transverse cross-section. Depending on the radial length of the penetrating segments, simultaneous pressing of a number of grooves 31 along the circumference of the tampon blank may generate a highly compressed core 33 of absorbent material, from which relatively uncompressed ribs 32 extend radially outwardly. Optionally, the core 33 may be compressed to a smaller extent in the area of the withdrawal end 24 of the tampon 23 than in its remaining area, to yield a less compressed proximal portion of a greater diameter. This may prevent leakage of body fluids when the tampon is emplaced. Next, the tampon preform as obtained by the above pressing may be subjected to further radial pressure on its outer circumference to finalize the circumferential surface of the ribs 32. In known procedures, the circumferential surface of the ribs 32 of the tampon preform is often pressed such that the grooves 31 are eventually enclosed, essentially forming channels, and the final tampon 23 acquires an essentially flat cylindrical outer circumference. In the present invention, it may be preferable that the ribs 32 of the preform are pressed only to such an extent that the grooves 31 remain "open" along the outer circumference of the tampon 23, thus reducing the area of the outer surface 29 of the tampon 23 capable of contacting the respective structures of the applicator 1 during use of the assembly. Also, it may be preferred that the penetrating segments used to form the present grooves 31 are thicker than ones usually employed, such that wider grooves 31 are obtained and further pressing of the ribs 32 will not lead to "closure" of such wider grooves 31. Further, the constricted insertion end 35, e.g., a rounded or round dome shaped insertion end 35, may be formed by further pressing. The circumferentially extending, radially raised portion 37 may also be provided, e.g., by pressing the tampon blank and/or the tampon preform radially less in this portion. Optionally, the tampon blank may be provided with a liquid-permeable sheathing, such that this is pressed simultaneously with the grooves.

Figure 2A:
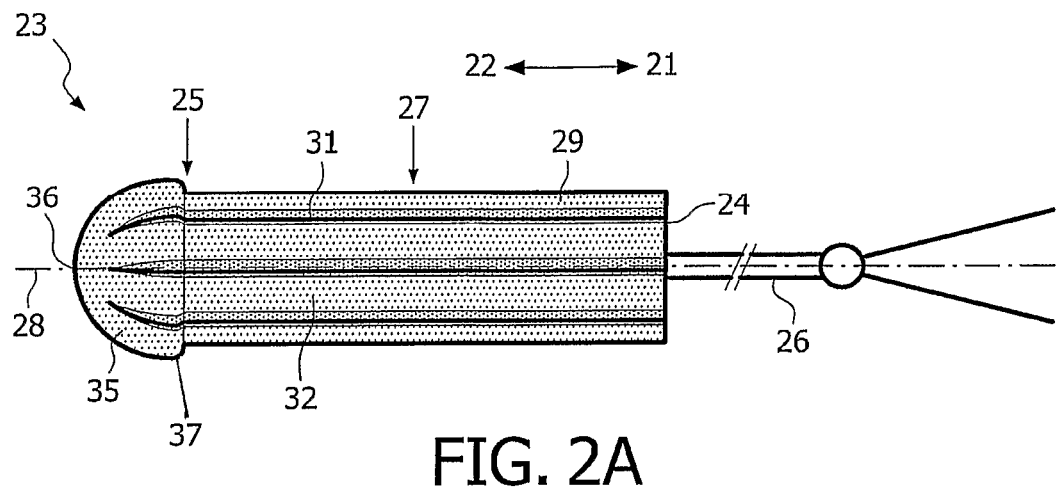
FIG. 2A illustrates a side view of an exemplary embodiment of a tampon suitable for use in the assembly of the present invention. The tampon is mushroom-shaped and is provided with circumferentially "open" longitudinal grooves.
Figure 2B:
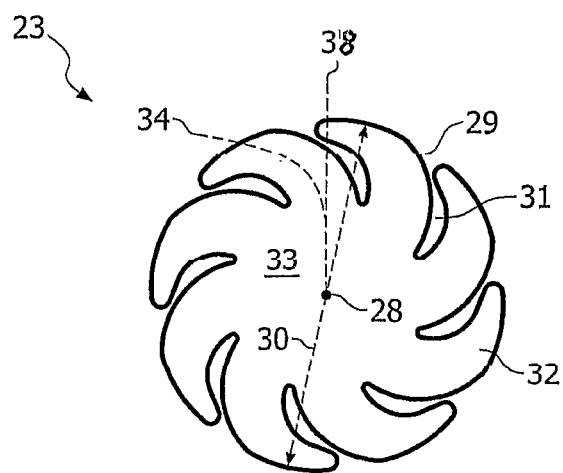
FIG. 2B illustrates a transverse cross-section through the central section of a tampon suitable for use in the assembly of the present invention.

A suitable process for producing tampons with grooves 31 defining interposed ribs 32, the pressing apparatus, and the resulting tampons, for use in the present assembly, are described in an earlier filed, not yet public patent application EP 04447289.2, herein incorporated by reference, and a cross-section of an exemplary embodiment of such tampons is shown in FIG. 2B. Such tampons comprise at least three ribs 32 defined by grooves 31, characterised in that at least one rib, in transverse cross-section, has a median 34 at least partially diverging from its radius 38. As used herein to describe this type of tampons, the term "radius of the rib" refers to the straight radial line that starts at the centre of the transverse cross-section of the tampon and runs towards its circumference through the point where the median of the rib crosses a fictive circle formed by the internal extremes of the grooves. The radius of a rib 38 and the median of a rib 34 are illustrated in FIG. 2B.

The present tampon 23 usually further comprises a withdrawal string 26 attached to its withdrawal end 24 to facilitate withdrawal of the tampon 23 after use. The withdrawal string 26 may be preferably flexible, hydrophobic, and strong enough in tension to resist breaking during removal of the product. It may be made of any of the materials used for withdrawal strings 26 in the art. It should be long enough. It can be a single cord, a tape, or a plurality of strings. Materials, which have worked well as the withdrawal string 26, are a hydrophobic cotton string, a hydrophobic polyester string or a mixture hereof. Polyester may make the string stronger. The withdrawal string 26 can be secured to the tampon in any manner well known to those of ordinary skill in the art.

The present tampon 23 optionally comprises a constricted insertion end 35, i.e., an insertion end 35 having a smaller diameter in transverse cross-section than the diameter of the central section 27 of the tampon 23. The diameter of the insertion end 35 may be greatest adjacent to the central section 27 of the tampon and may further decrease gradually in the distal direction 22. For example, the constricted insertion end 35 may be conical or rounded, and may preferably have a rounded dome shape. Because the insertion end 35 is the first portion of the tampon 23 to enter the vagina when the tampon 23 is ejected from the applicator 1, provision of a constricted insertion end 35 provides for a smoother insertion of the tampon 23, since the insertion end 35 may gradually displace the surrounding tissue and therefore cause less friction. Further, the constricted insertion end 35 may enable the tampon to be inserted deeper into the vagina, i.e., closer to the cervix, which may advantageously promote wetting of the tampon, since the origin of the fluid to be collected is deep in the vagina. Tampons having a constricted insertion end 35, in particular a rounded or round dome shaped insertion end 35, are therefore generally preferred by the consumer. The constriction or rounding of the insertion end 35 is normally done during the compression of the absorbent material to form the tampon 23. As an example, the axial length of the constricted insertion end 35, e.g., a rounded or round dome shaped insertion end 35, may range from about 2 mm to about 25 mm.

In an embodiment, the grooves 31 provided on the outer surface 29 of the tampon 23 may extend into the constricted insertion end 35. The grooves 31 may reduce the contact between the surface of the constricted insertion end 35 of the tampon and the petal sections 5 of the outer tube 3 during the ejection step. The reduced contact may advantageously decrease the disruption of the surface of the insertion end 35 by the petal sections of the outer tube 3 which may occur during the ejection step. Such disruption of the surface of the insertion end 35 may cause release and loss of fibre material from the insertion end 35 during the ejection step.

This may be particularly important, because the insertion end 35 may often be less compressed than the remainder of the tampon 23 and often may not be provided with any sheathing on its surface, and therefore may be more susceptible to disruption of its outer surface in use of the assembly.

The grooves 31 may extend all the way to the distal extreme 36 of the constricted insertion end 35 or may extend only partially into the constricted insertion end 35 and terminate before reaching the distal extreme 36 of the insertion end 35. For example, the grooves 31 may gradually taper in their depth and/or width toward the distal extreme 36 of the constricted insertion end 35. In general, the grooves 31 need not extend to the distal extreme 36 of the constricted insertion end 35 as this faces the central opening 8 in the outer tube 3 and usually does not come into contact with the petal sections 5 during the ejection step. Moreover, it may be preferable for injection into the vagina that the most distal portion 36 of the insertion end 35 is smooth.

Absorbent fibrous material usable in the tampon according to the invention may consist of any absorbent material having acceptable absorbency and modulus of elasticity properties that is capable of absorbing and/or retaining liquid. The absorbent structure can be manufactured in a wide variety of sizes and shapes and from a wide variety of liquid-absorbing materials. It is, of course, desirable to use absorbent materials having a minimum content of extraneous soluble materials since the product may be retained in the body for a considerable period of time. Retained soluble extraneous materials could cause a safety hazard if they are toxic, irritant, or sensitive. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibres; synthetic materials, such as polyester fibres, polyolefin fibres, absorbent foams, e.g. a flexible resilient polyurethane foam, absorbent sponges, super-absorbent polymers, absorbent gelling materials; formed fibres, such as capillary channel fibres and multi limbed fibres; synthetic fibres, or any equivalent material or combinations of materials, or mixtures of these.

In an preferred embodiment, the absorbing capacity of the present tampon may be further improved by selecting more absorptive material. When using material that absorbs more, the tampons are less voluminous, thus facilitating easier insertion and, especially when the tampon is not saturated, withdrawal of the tampon. Therefore, fibrous material usable in the tampon according to the invention may comprise more absorptive materials such as e.g. open-celled foam. The use of more absorptive material will also further reduce the risk of leakage and by-pass.

A tampon of the invention may optionally be provided with one or more markings on the surface. A marking may be provided by any mean means including printed using inks, or by impression. A marking may comprise any features including alpha numerals, graphic illustrations, patterns and/or photographic illustration. A marking may be, for example, information such as expiry date, absorbent capacity, use instruction, warning indications. Where a tampon is provided with information, it is an information carrier. A marking may also be advertising. A marking may provide product appeal to the user or groups of users. For example, it may comprise images, patterns, graphics or alpha numerals designed to appeal to a mind set of a user group by way of aesthetic appearance and/or life-style association (e.g. cartoons, logos etc.).

A tampon of the invention may optionally be provided in one or more colours. Colours may be printed as mentioned above, or impregnated into the material. A colour may indicate an expiry date, an absorbent capacity, a size or other information regarding the product. A colour may be designed to appeal to a mind set of a user group by way of aesthetic appearance and/or life-style association.

A tampon of the invention may optionally be provided with chemical indicator that is capable of indicative colour change. Such indicator may show, for example, a medical condition. The chemical indicator may react within one or more agents in bodily fluids to indicate an abnormality. For example, a chemical indicator may change colour when a subject is suffering such as anemia (by detecting iron/haemoglobin density), diabetes (by detecting glucose), position in the menstrual cycle (by detecting hormones), the presence of sexually transmitted diseases (by detecting antigens towards for example, gonorrhea, syphilis, hepatitis A, B or C, herpes, HIV, chlamydia) etc.

In an embodiment, the surface of the tampon 23 may be at least partially provided with a liquid-permeable sheathing. The sheathing provides a smoother surface which decreases the friction between the tampon surface 29 and the respective structures of the applicator 1 during the use of the assembly. By reducing the friction, the sheathing facilitates easier withdrawal of the ejector tube 12 and decreases the likelihood of proximal displacement of the tampon 23 during the cocking step. Moreover, the sheathing also protects the underlying fibrous material of the tampon 23 against disruption by the respective structures of the applicator 1 during use of the assembly. This decreases the chance that fibres would be released from the outer surface 29 of the tampon 23 during use of the assembly and thereby reduces the likelihood of loss of tampon material. Hence, provision of the sheathing further helps to solve the problems of prior art assemblies.

In an embodiment, the sheathing may be provided on the tampon blank before this is pressed to introduce areas of radial depression, in particular grooves 31, to the outer surface 29 of the tampon 23. Hence, areas on the tampon blank provided with the sheathing will be pressed radially to form the grooves 31 and, as a result, the sheathing will cover the surfaces of both the grooves 31 and the ribs 32 of the tampon. In this embodiment, the contact between the tampon 23 and the respective structures of the applicator 1 is reduced during use of the assembly due to the presence of the grooves 31 on the outer surface of the tampon 23. Moreover, the sheathing reduces the friction between the circumferential surface of the ribs 32 (i.e., areas of the tampon surface 29 which do contact the respective structures of the applicator 1) and respective structures of the applicator 1 during use of the assembly. Further, the sheathing also protects the tampon surface against the release of fibre material.

The sheathing typically does not decrease the absorbency, suction capacity or the expansibility of the tampon 23. The use of sheathings on tampons is well known in the art, as are suitable materials for such sheathings and methods to provide tampons with such sheathings. An exemplary disclosure of these aspects can be found in U.S. Pat. No. 4,816,100. For example, the sheathing may consist of an airlaid nonwoven covering material made of tangled, at least in part thermoplastic, heatsealing fibres or of a perforated plastic film, such as a three-dimensional apertured film, or the like. To maintain the absorbing capacity and expansion capacity of the tampon, said sheathing may preferably be a stretchable or elastic liquid-permeable sheathing.

Usually, the sheathing is not provided at the insertion end 35 of the tampon in order to provide better access of the menses to said insertion end 35.

In another embodiment, the tampon 23 further comprises a radially raised, circumferentially extending portion 37 which is provided proximally adjacent to the insertion end 35. The maximum outer diameter of said radially raised portion 37 is greater than the maximum outer diameter 30 of the central section 27 of the tampon 23, or at least of the part of the central section 37 proximally adjacent to said radially raised portion 37. For example, the maximum outer diameter of said radially raised portion 37 may be between 0.1 mm and 5 mm greater than the maximum outer diameter 30 of the central section 27 proximally adjacent to said portion 37. The radially raised portion 37 is usually formed during the compression of the absorbent material to form the tampon. Hence, the tampon blank is compressed radially less where the radially raised portion 37 is to be located. The axial width of the radially raised portion may be, e.g., between about 0.5 mm and about 7 mm. Hence, the circumferentially extending, radially raised portion 37 may be a continuous radially raised ring or may be formed by a plurality of circumferentially aligned, radially raised protrusions.

The radially raised portion 37 of the tampon 23 is thus configured to overlap radially with the projections 10 on the distal inner surface of the outer tube 3. Hence, the radially raised portion 37 of the tampon 23 is adapted to engage or interlock with the projections 10 on the outer tube 3, thereby preventing the displacement of the tampon 23 in proximal direction 21 during withdrawal of the ejector tube 12 from the outer tube 3 over the stored tampon 23.

Moreover, when the assembly is prepared for use, the tampon 23 may be disposed in the distal end 13 of the ejector tube 12 such that the inwardly flexible fingers 14 of the ejector tube 12 abut the proximal boundary 25 of the radially raised portion 37 of the tampon 23 and define an opening which has a smaller diameter than said radially raised portion 37 (as in FIGS. 3A and 3B). In this configuration, the radially raised portion 37 and the insertion end 35 of the tampon protrude from the distal opening of the ejector tube 12, while the remainder of the tampon is disposed within the ejector tube 12. The engagement of the fingers 14 against the proximal boundary 25 of the radially raised portion 37 prevents the tampon 23 from reentering the ejector tube 12 and thereby maintains the proper positioning of the tampon 23 within the assembly.

In an embodiment, the grooves 31 may extend into the radially raised portion 37, and further through this portion 37 into the insertion end 35. In such case, the orientation of the tampon 23 in the assembly will preferably be such that the projections 10 of the outer tube 3 do not become located within the grooves 31, as this would compromise the engagement between the projections 10 and the radially raised portion 37. To avoid orientation problems, e.g., the number of protrusions 10 may be at least one more than the number of grooves 31, or the grooves 31 may be spiral or helical, or the thickness of the inward projections 10 in the circumferential direction may be greater than the width of the grooves 31 of the tampon 23.

In an embodiment, the radially raised portion 37 of the tampon 23 is continuous with the constricted insertion end 35. For example, the radially raised portion 37 may have the greatest maximum outer diameter at its proximal boundary 25 and said diameter may further gradually decrease in the distal direction 22. Here, the proximal boundary 25 of the radially raised portion 37 would form a base of a rounded enlarged head of the tampon 23. Such tampon would have a "mushroom shape", i.e., the tampon 23 may be mushroom-shaped. The enlarged head may be, e.g., quasi-spherical, or may be axially prolonged or flattened.

Alternatively, the radially raised portion 37 may maintain a relatively uniform maximum outer diameter over a particular axial length, e.g., 0.5 mm to 5 mm and may then continue into a constricted insertion end 35. Such tampon would have a "rivet shape", i.e., the tampon 23 may be rivet-shaped. The insertion end may be, e.g., quasi-spherical, or may be may be axially prolonged or flattened.

A tampon 23 according to the present invention may take various dimensions and sizes. For example, the length of the tampon 23 may range between 20 mm and 70 mm, preferably between 35 mm and 60 mm, and more preferably up to 55 mm. For example, the weight of the tampon 23 may range between about 1.5 g and 6.5 g.

Accordingly, in view of the above description, in an embodiment the present invention provides an assembly comprising:

a compact tampon applicator 1 made of at least partially flexible material, such as plastic, and comprising an ejector tube 12, an outer tube 3 dimensioned to fit closely and telescopically over said ejector tube 12 and having a distal discharge end 4, a restraining means 2 between said tubes 3,12 for preventing the disassembly of said ejector tube 12 from said outer tube 3 in the proximal direction 21, and one or more inward projections 10 formed along the inner circumference adjacent to the distal end 4 of the outer tube, and a tampon 23 having a longitudinal body defining a constricted insertion end 35, a withdrawal end 24, a central section extending there between 27, a longitudinal axis 28, and an outer surface 29, characterised in that said tampon 23 has the following features:

it consists essentially of compressed absorbent fibrous material, it has length between about 35 mm and about 60 mm, it has weight between about 1.5 g and about 6.5 g, and the outer surface 29 of the tampon 23 comprises at least three radially pressed longitudinal grooves 31 defining adjacent longitudinal ribs 32, wherein the outer circumferential surface of the ribs 32 defines the maximum outer diameter 30 of the tampon 23 in transverse cross-section of between about 8 mm and about 18 mm, and said longitudinal grooves 31 define areas on the outer surface 29 having a smaller diameter in transverse cross-section than said maximum outer diameter of the tampon 23, whereby the contact between the outer surface 29 of the tampon 23 and the ejector tube 12 and/or the outer tube 3 is reduced.

In another embodiment, the present invention provides a tampon applicator assembly comprising:

an ejector tube 12;

an outer tube 3 dimensioned to fit closely and telescopically over said ejector tube 12 and having a distal discharge end 4 and one or more inward projections 10 formed along the inner circumference adjacent to the distal end 4 of the outer tube 3;

a restraining means 2 between said tubes 3,12 for preventing the disassembly of said ejector tube 12 from said outer tube 3 in proximal direction 21;

a tampon 23 comprising a radially raised, circumferentially extending portion 37 provided proximally adjacent to insertion end 35 of the tampon, characterized in that said one or more inward projections 10 of the outer tube 3 are configured to interlock with said radially raised, circumferentially extending portion 37 of the tampon 23, thereby preventing the tampon 23 from being displaced in the proximal direction 21 when the ejector tube 12 is withdrawn from the outer tube 3 over the stored tampon 23.

In another embodiment, the present invention provides a tampon applicator assembly comprising:

an ejector tube 12;

an outer tube 3 dimensioned to fit closely and telescopically over said ejector tube 12 and having a distal discharge end 4 and one or more inward projections 10 formed along the inner circumference adjacent to the distal end 4 of the outer tube 3;

a restraining means 2 between said tubes 3,12 for preventing the disassembly of said ejector tube 12 from said outer tube 3 in proximal direction 21;

a tampon 23 capable of expanding widthwise upon absorption of fluid and comprising a radially raised, circumferentially extending portion 37 provided proximally adjacent to insertion end 35 of the tampon, and further comprising at least one area of radial depression on outer surface 29 of the tampon 23 characterized in that said one or more inward projections 10 of the outer tube 3 are configured to interlock with said radially raised, circumferentially extending portion 37 of the tampon 23, thereby preventing the tampon 23 from being displaced in the proximal direction 21 when the ejector tube 12 is withdrawn from the outer tube 3 over the stored tampon 23, and said at least one area of radial depression on the outer surface 29 of the tampon 23 is configured to reduce friction between the outer surface 29 of the tampon 23 and the ejector tube 12 when the ejector tube 12 is withdrawn from the outer tube 3 over the stored tampon 23.

In another aspect, the present invention further provides for use of the present assembly of a compact tampon applicator and a tampon to discharge said tampon. The tampon is in particular a catamenial tampon and may be discharged within a body cavity, in particular vaginal cavity. Thereby, the tampon may be placed within said cavity.

In another aspect the present invention also relates to methods of production of the present assembly and of its parts and to an apparatus for producing the present assembly and its parts.

What is claimed is:

1. An assembly comprising:

a compact tampon applicator made of at least partially flexible material, and comprising an ejector tube, an outer tube dimensioned to fit closely and telescopically over said ejector tube and having a distal discharge end, a restraining means between said tubes for preventing the disassembly of said ejector tube from said outer tube in the proximal direction, and one or more inward projections formed along the inner circumference adjacent to the distal end of the outer tube, and a tampon having a longitudinal body defining a constricted insertion end, a withdrawal end, a central section extending there between, a longitudinal axis, and an outer surface, wherein said tampon has the following features:

the tampon consists essentially of compressed absorbent fibrous material, the tampon has length between 35 mm and 60 mm, the tampon has weight between 1.5 g and 6.5 g, the outer surface of the tampon comprises at least three areas of radial depression comprising three radially pressed longitudinal grooves defining adjacent longitudinal ribs, wherein the outer circumferential surface of the ribs defines the maximum outer diameter of the tampon in transverse cross-section of between 8 mm and 18 mm, and said longitudinal grooves define areas on the outer surface having a smaller diameter in transverse cross-section than said maximum outer diameter of the tampon, whereby the contact between the outer surface of the tampon and the ejector tube and/or the outer tube is reduced, and an enlarged head comprising a radially raised, circumferentially extending portion proximally adjacent to the constricted insertion end, and a proximal boundary that forms a base of said enlarged head, wherein the base of the enlarged head of the tampon is configured to engage with the inward projections of the outer tube to prevent the displacement of the tampon in the proximal direction during withdrawal of the ejector tube from the outer tube over the tampon.

2. The assembly according to claim 1, wherein the one or more inward projections of the outer tube are between 0.2 mm and 5 mm thick in the circumferential direction.

3. The assembly according to claim 1, wherein said tampon comprises a core of compressed absorbent fibrous material from which said longitudinal ribs extend radially outward.

4. The assembly according to claim 3, wherein said longitudinal ribs are at least partially uncompressed compared with said core.

5. The assembly according to claim 1, wherein said longitudinal grooves are parallel to the longitudinal axis or are spirally or helically shaped in the direction of the longitudinal axis.

6. The assembly according to claim 1, wherein said longitudinal grooves extend between the insertion end and withdrawal end of the tampon.

7. The assembly according to claim 6, wherein said longitudinal grooves are spaced at regular circumferential angle intervals.

8. The assembly according to claim 1, wherein said longitudinal grooves extend into the constricted insertion end.

9. The assembly according to claim 1, wherein the outer surface of the tampon is at least partially provided with a liquid-permeable sheathing.

10. The assembly according to claim 1, wherein the tampon is capable of expanding widthwise upon absorption of fluid.

11. The assembly according to claim 1, wherein the tampon is mushroom-shaped.

12. The assembly according to claim 1, wherein the tampon is rivet-shaped.

13. A method to manufacture an assembly according to claim 1, comprising disposing said tampon within said tampon applicator.

14. A method for discharging said tampon of claim 1 comprising discharging the tampon within a body cavity.

15. The assembly according to claim 1, wherein said flexible material comprises plastic.

16. The assembly according to claim 1, wherein the axial width of the radially raised portion is between about 0.5 mm and about 7 mm.

17. The assembly according to claim 1, wherein the inward projections are disposed approximately at a base of petal sections of the outer tube.

18. The assembly according to claim 1, wherein the base of the enlarged head is approximately perpendicular to the longitudinal axis of the tampon.

19. The assembly according to claim 1, wherein a portion of the base has a flat surface.

20. The assembly according to claim 1, wherein the outer surface of the tampon includes a change in slope between the central section and the enlarged head.

21. The assembly according to claim 1, wherein the cross-sectional area of the tampon changes along the longitudinal axis of the tampon between the central section and the enlarged head.

* * * * *